United States Patent [19]

Sitte

[11] Patent Number: 4,563,883

[45] Date of Patent: Jan. 14, 1986

[54] SPECIMEN IMMERSING DEVICE

[75] Inventor: Hellmuth Sitte, Siefeld, Austria

[73] Assignee: C. Reichert Optische Werke AG, Vienna, Austria

[21] Appl. No.: 651,381

[22] Filed: Sep. 17, 1984

[51] Int. Cl.⁴ .............................................. F25B 19/00
[52] U.S. Cl. ..................................... 62/514 R; 62/64; 62/68; 62/373; 141/284; 366/169
[58] Field of Search ................ 62/78, 64, 381, 514 R, 62/68, 373; 141/284; 366/169

[56] References Cited

U.S. PATENT DOCUMENTS

| 2,875,588 | 3/1959 | Berger | 62/64 |
| 3,228,838 | 1/1966 | Rinfret et al. | 62/64 |
| 4,249,828 | 2/1981 | Condolios | 366/169 |

Primary Examiner—Ronald C. Capossela
Attorney, Agent, or Firm—Alan H. Spencer; S. Raines

[57] ABSTRACT

A device for immersing a specimen into a cryogenic cooling liquid comprising an injector for carrying a specimen, means for accelerating the injector to a predetermined velocity vertically into the liquid, and means for rotating the injector, before the vertical movement ends, or at the moment it ends, to promote heat transfer from the specimen. Various means for effecting rotation of the injector are described.

11 Claims, 6 Drawing Figures

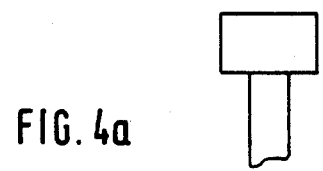
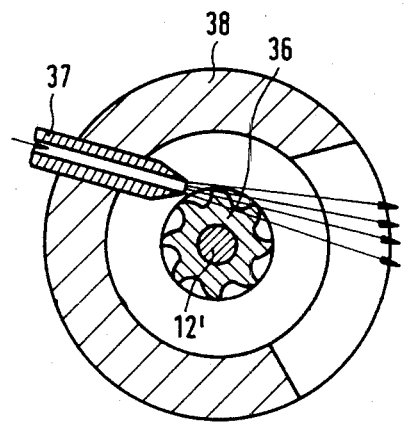

SPECIMEN IMMERSING DEVICE

BACKGROUND OF THE INVENTION

This invention relates to a device for immersing a specimen in a cryogenic-fixation liquid for subsequent examination by means of a microscope and, in particular, by means of an electron microscope.

Cooling liquids at temperatures between $-100°$ C. and $-190°$ C. are used for numerous specimen-preparation operations. Such liquids are particularly used for the shock-freezing or cryogenic-fixation of biological or medical specimens for subsequent examination by means of a microscope, and, in particular, for examination by means of an electron microscope. The object of a cooling operation of this nature is to abstract as much heat as possible from the specimen within the shortest possible time. This object is particularly important in the case of biological or medical specimens which have not been pretreated (that is to say, which have not been subjected to a preliminary fixation and/or freezing-protection treatment), since, for these specimens, the cooling rate alone determines whether artificial separation of the water-rich plasmatic phases takes place which would render meaningful microscopic or histochemical examination impossible. The cooling rate determines whether the specimen freezes to a true-to-life, glassy form ("vitrification" takes place at cooling rates greater than $10,000°$ C./sec.).

The high cooling rates of specimens which are required are obtained as a result of known injection procedures only in an extremely thin edge zone of the specimen, where the structure is, initially, well preserved and is cooled to below $-80°$ C. In contract, as a result of the poor heat-conduction capability of ice, zones which are situated deeper in the interior of the specimen, in particular inside comparatively large specimens with diameters in excess of 3 mm, generally remain, at temperatures which lie considerably above the critical limiting value of $-80°$ C. Complete stabilisation of the fine structures and low-molecular constituents of these specimens is, therefore, not effected. Portions of the injection apparatus, which is generally made of metal, likewise remain at a comparatively high temperature.

Inadequate cooling of a specimen could be countered by using cooling baths containing columns of liquid of sufficient height to permit the specimens to be moved, generally vertically, over distances of between 50 and 100 cm. By this means, an injection of a specimen at a velocity of 5 to 15 m/sec would be prolonged by a period of time ranging from 300 m/sec to 2 sec, which suffices, as a rule, for the complete cooling and stabilisation of specimens. Practical considerations such as the ease of handling and the safe operation of injection apparatus, have lead in practice to the depth of cooling baths being limited to approximately 10 cm. For an average injection velocity, the injection into a 10 cm. cooling bath is completed after only 100 m/sec. This period of time is sufficient for the vitrification of a thin edge zone, but is insufficient for the complete freezing of comparatively large specimens.

The specimen is necessarily brought to rest following the completion of the known injection operations, which leads very quickly, to heating of the edge zone of the specimen, after the edge zone has been cooled to temperatures near the original temperature of the cooling bath. The heating of the specimen is caused by the establishment of a temperature gradient in the cooling liquid. During this heating, a secondary change occurs in the frozen specimen as the limiting value of $-80°$ C. is exceeded, this change altering the previously stable condition.

If it is desired to cut specimens, in the amorphous/vitrified condition, on a cryogenic-microtome, and in particular on a cryogenic-ultramicrotome, a temperature of $-140°$ C. must not be exceeded in the edge zones, which cannot be guaranteed if the specimen suddenly comes to rest 100 msec after the beginning of the injection operation. In order to preserve the true-to-life vitrification initially obtained in the course of the rapid injection movement, it is necessary to use appropriate measures to restrict, to the greatest possible extent, the establishment of a temperature gradient which is formed as a secondary effect immediately after the specimen has come to rest, in the cooling liquid which is directly adjacent to the exposed surface of the specimen.

OBJECTS OF THE INVENTION

An object underlying this invention is to provide a device which prevents or restricts the establishment of harmful temperature gradients after the specimen has come to rest in the cooling liquid, following the injection operation. If the establishment of temperature gradients is sufficiently restricted, no secondary artificial changes occur in the specimen, which would otherwise reduce the quality of the state of preservation of the specimens, and thereby render the subsequent examination by means of a microscope, of questionable value.

BRIEF DESCRIPTION OF THE INVENTION

According to the present invention, there is provided a device for immersing a specimen into a cryogenic cooling liquid comprising an injector for carrying a specimen, means for accelerating the injector to a predetermined velocity vertically into the liquid, and means for rotating the injector, before the vertical movement ends, or at the moment it ends, to promote heat transfer from the specimen.

The device provides a simple means for ensuring that the flow of heat from the speciment into the cooling liquid continues to an extent such that recrystallisation of the edge zone of the specimen, which has initially frozen amorphously or as microcrystals, is prevented.

In a first embodiment of the invention, the rotating means comprises a rotatable sleeve which is arranged concentrically with a corresponding cylinder on the injector, the internal diameter of the sleeve being slightly larger than the external diameter of the cylinder whereby rotation is transmitted by friction in air between the sleeve and the cylinder. With this embodiment the injection movement causes the cylinder to enter the space defined by the sleeve. Since the injector is freely rotatable and the air-gap between the facing cylindrical surfaces is appropriately small, the air friction between the two cylindrical surfaces causes the injector to rotate.

Rotation of the injector and specimen in the cooling bath causes convection currents in the cooling liquid, both adjacent the surface of the specimen and in the cooling bath as a whole. As a result, temperature gradients are prevented from being formed in those regions of the cooling liquid in direct proximity to the surface of the specimen. Flow of the cooling liquid in the cooling bath causes an evening-out of the temperature difference between the injector and the cooler walls of the cooling bath, which are suitably composed of metal.

In a second embodiment of the invention the rotating means comprises a rotatable driving disc, a driven disc and means for urging the driving disc into driving engagement with the driven disc. The formations may be a planar or a conical surface to provide a frictional coupling.

In a third embodiment of the invention, the rotating means comprises a gas jet and a turbine wheel.

Preferably convection generating elements are attached to the injector in the immediate vicinity of the specimen to generate convection currents in the cooling liquid when the injector is rotated.

In another embodiment of the invention the specimen may be mounted on a specimen carrier, the axis of the carrier being spaced from the axis of the injector so that the specimen carrier generates convection currents in the cooling liquid as the injector rotates.

Preferably a timing device is arranged to control the means for rotating the injector so that it rotates for a predetermined time.

The time period can be adjusted to suit different requirements, adjustments being effected by means of suitable setting means which may be of an analog or digital type.

BRIEF DESCRIPTION OF THE DRAWINGS

In the following text, illustrative examples of the invention are described with reference to the attached drawings, in which:

FIGS. 4a and 4b are diagrammatic longitudinal and cross-sections of another means for providing rotary movement of the injector.

DETAILED DESCRIPTION OF THE DRAWINGS

Figure 1:
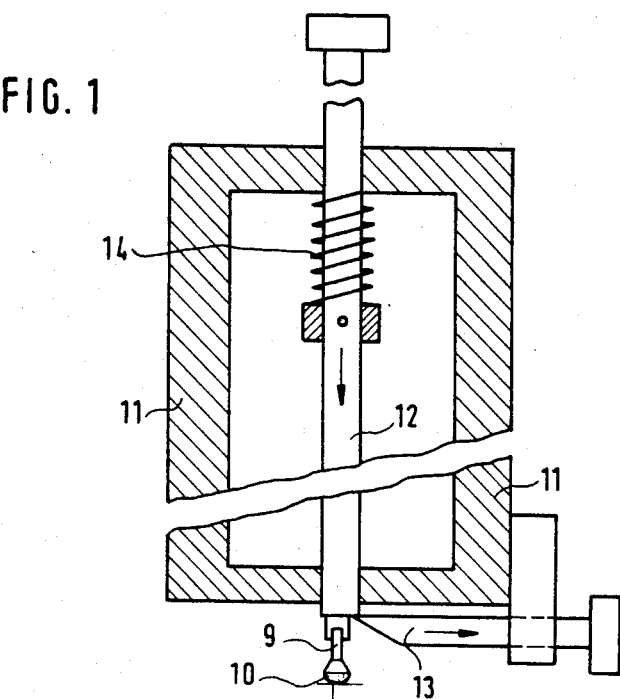
FIG. 1 shows a diagrammatic cross-section of an injection arrangement including a cooling bath.
Figure 1:
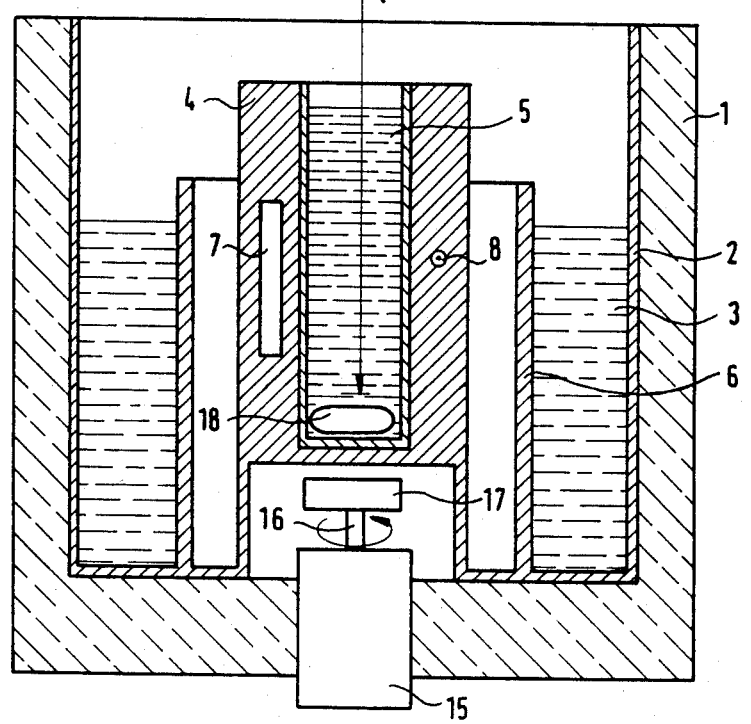

The system shown in FIG. 1 shows the current state of the art. Liquid nitrogen 3, as the cryogen for cooling the metal cylinder 4, is contained in a reservoir 2 which is surrounded by insulation 1. A cooling medium 5 (e.g. a liquefied halogenated hydrocarbon, or liquefied ethane, propane, or isopentane) is in the metal cylinder 4. The sleeve 6 prevents direct contact between the liquid nitrogen 3 and the metal cylinder 4, thus permitting this cylinder to be counter-heated, by means of the heater cartridge 7, to a minimum temperature which is predetermined by the freezing point of the cooling liquid 5, and which is measured by means of a temperature sensor 8.

The injection of the biological or medical specimen 10, which is fastened to a specimen carrier 9, is effected by means of an injector 12 which is vertically guided in the portion 11, and which executes a vertically downward movement once the trigger 13 has been operated. This downward movement is generated by means of a compression spring 14, or by other equivalent means such as a gas spring, to provide an acceleration of between 5 and 15 m/sec which experience has shown to be necessary for satisfactory vitrification or cryofixation.

After travelling a length "L", the injector 12, with the specimen 10 on the holder 9, comes to rest. Under normal conditions, this rest condition also cancels the relative movement between the cooling liquid 5 and the exposes surface of the specimen 10, which leads directly to the establishment of a temperature gradient in the directly adjacent cooling liquid. As a result of this temperature gradient, the temperature in the marginal layers, which have perfectly vitrified, commences to rise within a few milliseconds, especially with specimens of large diameter e.g. in excess of 3 mm.

Insofar as the temperature in this zone rises above $-135°$ C., the watery plasmatic matrix of the specimen, which has initially been vitrified to an amorphous mass, crystallises and, as a result, comparatively high-resolution examination in an electron microscope is no longer feasible. If the temperature rises above the range centered on $-80°$ C., small molecules and ions begin to redistribute themselves, and this redistribution makes it impossible to draw histochemical conclusions on the basis of an element analysis (EDX or LAMMA), or on the basis of autoradiography.

Various attempt have been made to agitate the cooling liquid by means of a stirring device, for example a magnetic stirrer, comprising a drive motor 15, a magnet 17 which is fastened to the drive shaft 16 of this motor, and a stirring magnet 18 which rests on the bottom of the cooling bath. However, this arrangement gives rise to only low flow velocities in the cooling liquid 5, which are insufficient for the required effect. Satisfactory cryofixation can be ensured, by a method wherein the length "L" of the injection channel is increased from the range of approximately 10 cm customarily used to approximately 5 to 10 times this amount. However, this method creates problems relating to the cooling of the high column of cooling medium, and to the thermostatic control of its temperature, as well as in connection with the design of the injector. Apart from these problems, increasing the length of the injection travel increases the manufacturing cost of systems of this type, increases the operating costs by a substantial margin, and considerably complicates their operation.

Figure 2:
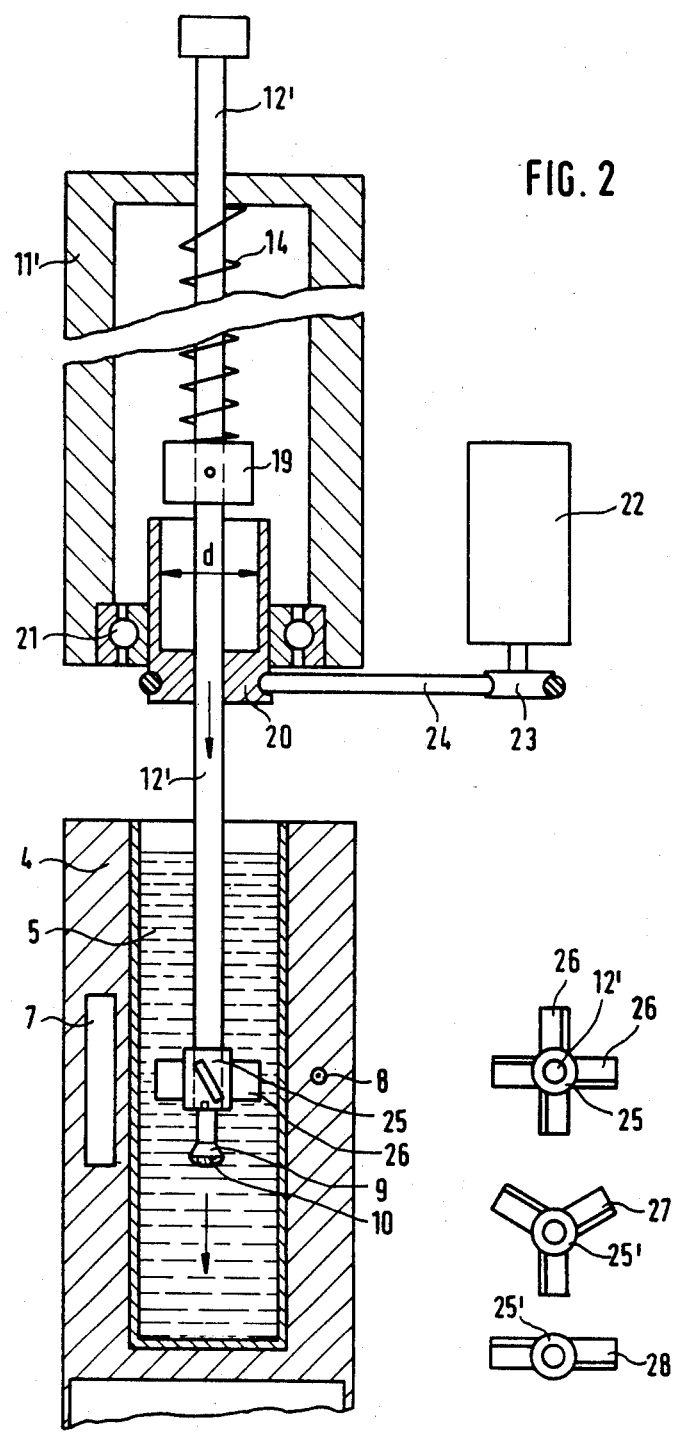
FIG. 2 is a diagrammatic cross-section of a system with a driving sleeve and a propeller for generating convection in the cooling liquid.
Figure 3B:
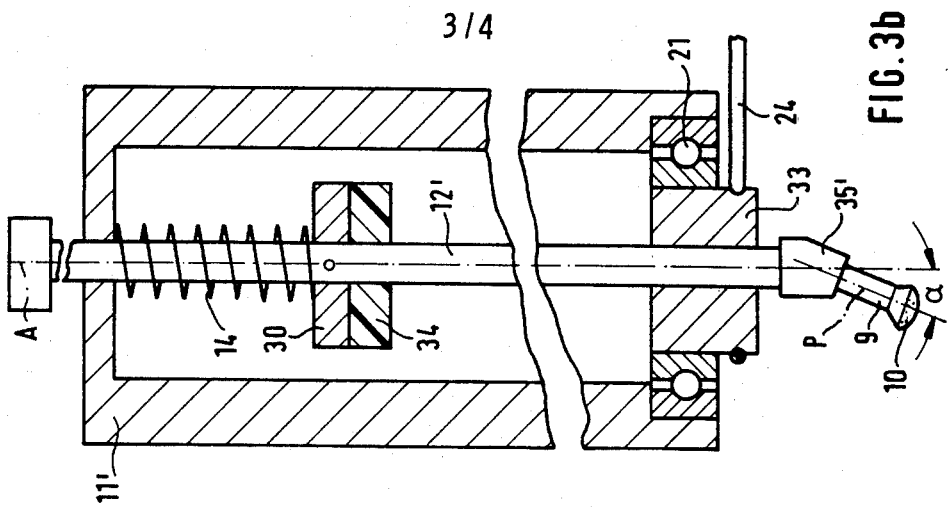
FIGS. 3a and 3b are diagrammatic cross-sections of portions of two rotating means for the injector.
Figure 3A:
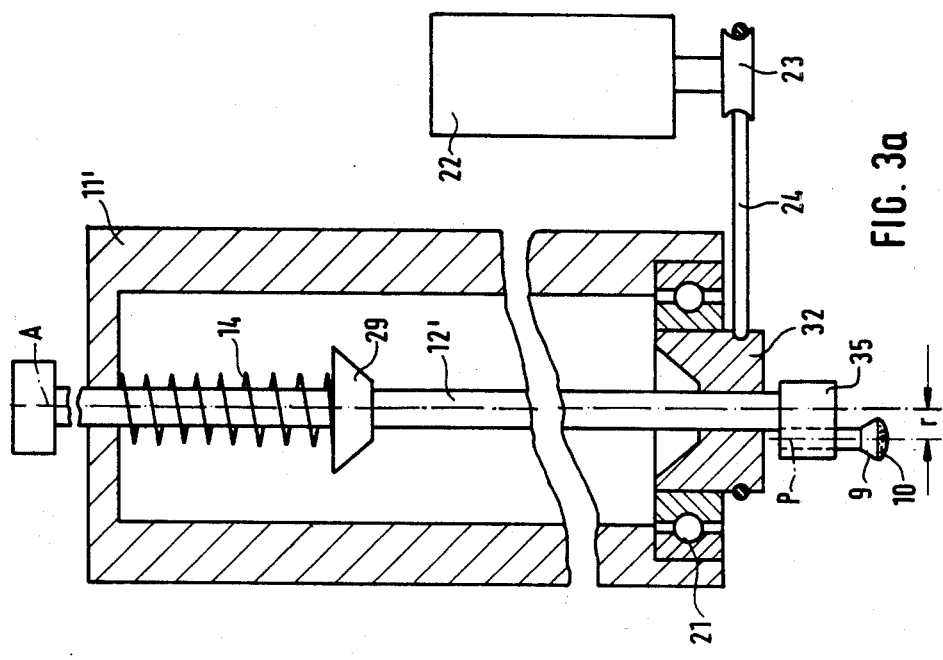

The inadequacies of the known devices for the cryofixation of comparatively large specimens with diameters in excess of 3 mm by means of rapid immersion in a cooling liquid can be eliminated, in a simple manner, by means of a system according to the invention, this system being represented in FIGS. 2 to 4. For this purpose, FIG. 2 shows that, instead of the injector arrangement shown in FIG. 1, an injector, 12', is located in a guide element 11', in a manner permitting vertical displacement, a cylindrical body 19 being fastened, coaxially to the injector. The outer diameter of the cylindrical body 19 is only slightly smaller than the inside diameter "d", of the sleeve 20 through which the injector 12' passes, with adequate clearance, so that when the sleeve is rapidly rotated in the ball-bearing 21, e.g. by means of an electric motor 22 and a transmission 23/24, the cylinder 19 is also driven by friction within the air entrained between the corresponding surfaces of the parts 19 and 20. At the same time, the cylinder 19 and the sleeve 20 cause the injection movement to be pneumatically damped, as a result of which the end of this movement is not abrupt, but occurs in the course of a smooth deceleration.

As shown in FIG. 2, a further development of the system involves the fastening of small propeller blades, in a symmetrical arrangement, to the assembly element 25 which serves, inter alia, for attaching the specimen holder 9 to the injector 12'. This embodiment is particularly advantageous for the injection of a rotationally-symmetrical specimen holder 9 and specimens 10. At the same time, it is possible, within the scope of the invention, to install four blades 26 of this type (compare the cross-section, the side view, and the plan view), three blades 27 of this type, two blades 28 of this type, or a larger number of blades of this type, which are arranged, in all cases symmetrically around the injector rod 12' on the intermediate piece 25 or 25'. The propeller blades 26/27 28 cause the cooling medium to circulate at the speeds which are used (above 10 revolutions/sec), that adequate convection occurs at the surface of the specimen.

As shown in FIG. 3, a further development of the invention comprises the attachment to the injector 12' of a cone 29, or a plate 30, instead of a cylinder. The cone or plate is pressed against the rotating opposing surface of the part 32 or 33, by the force of the spring 14, thereby bringing about a driving action in the manner of a clutch plate. If desired coatings 34 which promote the driving effect, and/or resiliently buffer the vertical injection movement may be provided.

As shown in FIG. 3, further embodiments can comprise the installation of rotationally-symmetrical specimen holders 9, or approximately rotationally-symmetrical specimens 10, on the injector 12', via an intermediate piece 35/35', so that the specimen assumes a position which is eccentric with respect to the longitudinal axis A of the injector 12'. When the injector rotates it causes the specimen 10 to move relative to the cooling liquid 5. At the same time, the intermediate piece 35 can offset the longitudinal axis P of the specimen carrier 9 by an amount "r" with respect to the axis A of the injector 12', this amount corresponding to the radius of eccentricity of the movement. Alternatively, the axis P of the specimen carrier 9 can be arranged so that it is tilted relative to the axis A of the injector 12', through the angle α, thereby bringing about the desired eccentric position of the specimen 10. In both cases, the specimen 10 on the holder 9 executes a rotary movement in the cooling liquid 5 when the drive 22/23/24 rotates.

Finally, as shown in FIG. 4, a further embodiment of the invention can take a form wherein the rotation of the injector rod 12' is not brought about by means of a motor and a transmission, but by means of a bucket wheel 36, in the manner of a gas turbine. The bucket wheel 36 is attached to the injector 12' and the turbine is caused to rotate by means of a stream of gas which enters the part 38 via a jet nozzle 37, the rotation starting before the injector 12' is brought to rest by means of the pneumatic damping created by two corresponding cylindrical surfaces 39/40.

It is possible, within the scope of the invention, to introduce modifications with respect to the illustrative embodiments which have been described above by reference to FIGS. 2 to 4. It is thus possible to manufacture the system according to the invention in various technically advantageous variants, in that several elements which have been described individually are integrated together, or are combined in a manner which differs from the representation and description in the illustrative embodiments. This applies, for example, in the case of the transmission or the production of the rotary movement of the injector, which can be accomplished, in a number of ways (e.g. by means of a magnetic coupling, by designing the injector rod as a motor armature and installing the motor winding on the injector housing, by an eddy-current unit, via a direct, geared coupling, etc.).

Similarly elements which bring about efficient convection of the cooling liquid can be produced in a variety of designs, other than the examples given in FIGS. 2 to 4. It is important that the injector be caused to execute a vigorous rotary movement before the end of its vertical injection movement, or at the moment this vertical movement ends, but this rotary movement can be produced by any suitable means. Furthermore the injection of the specimen 10 can be effected by means of a spring element 14, pneumatically, by gas pressure, or by equivalent means.

I claim:

1. A device for immersing a specimen into a cryogenic cooling liquid comprising a holder for carrying a specimen, means for injecting said holder at a predetermined velocity downwardly into the liquid, and means for rotating the holder while in said liquid.

2. The device of claim 1 wherein said injection means includes an axially displaceable shaft, said holder being mounted on one end of said shaft, said rotating means includes a rotatable member having a bore, said bore being adapted to receive said shaft, said member being adapted to transfer rotational motion of said member to said shaft and drive means to rotate said member.

3. The device of claim 2 wherein said member and said shaft are frictionally coupled.

4. The device of claim 3 wherein said injection means includes a biasing means, said biasing means being adapted to store sufficient energy to accelerate said shaft to a velocity of 5 m/sec, and trigger means to release the energy of said biasing means.

5. The device of claim 4 wherein said biasing means urges said shaft and said rotatable member into frictional engagement.

6. The device of claim 4 wherein said biasing means includes a spring.

7. The device of claim 4 wherein said drive means includes a timing control.

8. The device of claim 4 wherein a plurality of fluid impellors are mounted on said shaft.

9. The device of claim 8 wherein said drive means includes a fluid jet and turbine operatively associated therewith.

10. The device of claim 8 wherein said drive means includes an electric motor operatively connected to said shaft.

11. The device of claim 4 wherein said rotatable member has a hollow cylindrical sleeve extending therefrom and said shaft has a cylinder mounted thereon, said cylinder having an outer surface adapted to cooperate with the inner wall of said sleeve whereby frictional engagement is provided by the air between said sleeve and said cylinder.

* * * * *